United States Patent [19]

Tobler et al.

[11] Patent Number: 5,406,084
[45] Date of Patent: Apr. 11, 1995

[54] PROCESS AND DEVICE FOR THE IN-LINE NIR MEASUREMENT OF POURABLE FOODSTUFFS

[75] Inventors: Hans Tobler, Algetshausen; Peter Perten, Sarnen, both of Switzerland

[73] Assignee: Buhler AG Maschinenfabrik, Uzwil, Switzerland

[21] Appl. No.: 960,451
[22] PCT Filed: Apr. 23, 1992
[86] PCT No.: PCT/CH92/00080
  § 371 Date: Feb. 22, 1993
  § 102(e) Date: Feb. 22, 1993
[87] PCT Pub. No.: WO92/18864
  PCT Pub. Date: Oct. 29, 1992

[30] Foreign Application Priority Data
  Apr. 23, 1991 [CH] Switzerland .......... 9101220

[51] Int. Cl.⁶ .............................. G01N 21/35
[52] U.S. Cl. ............ 250/339.01; 250/339.12; 250/341.1; 250/910
[58] Field of Search ......... 250/339, 341, 343, 359.1, 250/339.12, 339.02, 339.11, 339.01, 341, 343, 359.1, 910

[56] References Cited

U.S. PATENT DOCUMENTS

| | | |
|---|---|---|
| 3,776,642 | 12/1973 | Anson et al. . |
| 4,040,747 | 8/1977 | Webster ............ 356/188 |
| 4,260,262 | 4/1981 | Webster . |
| 4,286,237 | 8/1981 | James . |
| 4,400,086 | 8/1983 | Webster ............ 356/36 |
| 4,404,642 | 9/1983 | Rosenthal . |
| 4,422,760 | 12/1983 | Webster ............ 356/244 |
| 4,466,076 | 8/1984 | Rosenthal . |
| 4,479,055 | 10/1984 | Perten ............ 250/343 X |
| 4,540,286 | 9/1985 | Satake et al. . |
| 4,563,581 | 1/1986 | Perten ............ 250/359.1 X |
| 4,640,614 | 2/1987 | Roberts et al. ......... 250/341 X |
| 4,734,584 | 3/1988 | Rosenthal . |
| 4,742,228 | 5/1988 | Bischoff . |
| 4,752,689 | 6/1988 | Satake . |
| 4,866,644 | 9/1989 | Shenk et al. . |
| 4,883,963 | 11/1989 | Kemeny et al. ............ 250/339 |
| 4,963,743 | 10/1990 | Satake et al. . |
| 5,220,168 | 6/1993 | Adamski et al. ............ 250/339 |

FOREIGN PATENT DOCUMENTS

| | | |
|---|---|---|
| 0240185 | 10/1987 | European Pat. Off. . |
| 304232 | 2/1989 | European Pat. Off. . |
| 179108 | 7/1989 | European Pat. Off. . |
| 388082 | 9/1990 | European Pat. Off. . |
| 404562 | 12/1990 | European Pat. Off. . |
| 3024794 | 1/1982 | Germany . |
| 8500656 | 2/1985 | WIPO . |
| 8504957 | 11/1985 | WIPO . |

OTHER PUBLICATIONS

"Near-Infrared Reflectance Analysis", Analytical Chemistry, vol. 55, No. 12, Oct. 1983, by D. Wetzel, pp. 1165A–1176A.
"Characteristics Of Non-Destructive Near-Infrared Instruments For Grain And Food Products", 1985 Meeting Japan Food Science Institute, by Robert D. Rosenthal, pp. 1–23.

*Primary Examiner*—Constantine Hannaher
*Assistant Examiner*—Edward J. Glick
*Attorney, Agent, or Firm*—Finnegan, Henderson, Farabow, Garrett & Dunner

[57] ABSTRACT

A new NIR measuring process and apparatus which can measure both floury commodities and whole kernels, and other constituents of pourable foodstuff products in-line. A large number of individual measurements are made with a measuring time per individual measurement of less than 100, preferably 50, milliseconds and these are statistically averaged by a computer. A rotating filter principle as well as the diode array principle can be used. For grain products, the protein, water and ash content can be determined with a high degree of accuracy. The measured values are directly usable, for the control and regulation of corresponding foodstuff parameters.

39 Claims, 4 Drawing Sheets

PROCESS AND DEVICE FOR THE IN-LINE NIR MEASUREMENT OF POURABLE FOODSTUFFS

FIELD OF THE INVENTION

The present invention relates to a process for the in-line NIR measurement of the constituents of pourable commodities. More particularly the present invention relates to a process and apparatus for the in-line NIR measurement of pourable food products.

BACKGROUND OF THE INVENTION

A large number of different measuring methods are known for this purpose such as the NMR measuring technique, microwave methods or capacitive methods. In practice, only a few have found widespread use, some for only the measurement of a single constituent.

Measuring the product moisture of whole grain kernels by means of microwaves is known. However, even more widespread in grain processing is the use of capacitive measurement as disclosed, for instance, in Applicant's commonly owned German reference 30 24 794. The determination of the water content of whole kernels, and also the regulation of the amount of moisturization to a specific water content, can be achieved with great precision by using this capacitive measurement.

Capacitive measurement uses a plate capacitor, that is, via an element of large area. For this purpose, the sample to be measured moves past the capacitor plates, which is ideal for an in-line measurement, that is, for a measurement in the product flow. By appropriate design of the measuring section, average sample values can be established.

A sample preparation is necessary for the on-line measurement of the moisture of flour and semolina using Near Infra-Red (NIR) Reflectance Spectrometer.

NIR measurement requires not only a light source but also an optical system which accordingly functions in the manner of a point measurement. As is known, every movement, be it the optical system or the sample to be measured, creates particular problems for the optical system and can cause the surface character to become unsharp.

This problem is satisfactorily resolved in that the product sample for NIR measurement not only is brought into a constant state, for example, as regards pressure and density, but the product sample is stopped, respectively, that is, it is arrested for the actual measurement such as in a laboratory measurement. The Applicant was able to introduce a corresponding measuring device (see European Patent Application No. 179 108) into practice with remarkable results. However, as a great drawback, it was found that the measurement of whole kernels, for instance, the protein content of whole grain kernels, is not possible with this process. In practice, this lead to the following measuring situation:
- the water content of the whole kernel is determined by the capacitive measuring technique or, if need be, the microwave measuring technique,
- the protein content of flour is measured with the above described NIR method,
- the protein content of whole kernels must, however, be determined in the laboratory.

Furthermore, many on-line, special measuring devices, for example, for product color, are currently available for intermediate mill products. However, in every case, a calibration with a calibrating specimen must be performed to be able to correct all interfering parameters.

Particularly disturbing, however, is the fact that 3 to 5 fundamentally different wavelength ranges, from gamma rays to microwaves, are used in one and the same production plant such as a mill. Thus, the measurement results frequently can be compared only with great difficulty even though the product, such as whole kernels, semolina or flour, is basically the same.

It is an object of the invention to eliminate at least a substantial portion of the described drawbacks and to make possible an in-line measurement without the requirement of sample removal from the production flow.

SUMMARY OF THE INVENTION

The solution according to the present invention is achieved by the following
- the product is conveyed in front of an NIR measurement recorder as a compact stream
- the wavelength range or ranges of the reflected light from a larger number of individual measurements are detected, the individual measurements being performed one after the other in time, and each individual measurement being performed for an entire spectrum of a moving sample with measuring times below 100, preferably below 50, milliseconds for a spectrum
- and the constituents are determined by statistical averaging of the relevant measurements and calculated on the basis of a calibration value.

Measured values can already be determined with great accuracy by means of an experimental device. This is surprising to the extent that the invention, from the traditional thinking in the laboratory: preparation of the sample, arresting of the sample, nevertheless completely solved the recording of several measured values from the same sample and the averaging thereof. All that is necessary is a compact, homogeneous stream, and thereby a reproducible condition of the sample surface. Of the sample itself all that is required is that the sample be moved relative to the measurement recorder, preferably forwards in the sense of the product flow. A large number of individual measurements are performed, however, on constantly changing sample material. Thus, different measurement values are thus consciously obtained.

It is important that a large number of individual measurements be made with measuring times below 50 milliseconds so that one or, if necessary, several constituents corresponding to the selected wavelength range or ranges can be calculated by statistical averaging.

It is thus averaged doubly, an averaging over time as well as over different specimen zones. In spite of the movement of the product and the very short exposure times, measured values of better quality than with previous methods can be obtained.

Particularly surprising, however, is the fact that, particularly for the measurement of whole kernels, values of high precision can be obtained for the constituents. It has nevertheless become possible therewith for the first time to determine, in-line, various constituents such as water, protein, ash, as well as product color, with the same system both for flour-like and granular products. However, with this, there is opened the possibility of measuring constituents in a mill from the storage of the whole kernels through the intermediate products to the finished products with one and the same measuring principle so that also, without difficulty, immediately comparable values are obtained. This greatly simplifies mill administration and, more than in the prior art, allows production to be assisted by suitable automatic means.

The new invention allows for a large variety of especially advantageous additional embodiments.

It is particularly preferred that the movement of the product in front of the NIR measurement recorder be continuous, and respectively, held constant. For individual product types, it is proposed that the measuring time of an individual measurement and the speed of movement of the product be-adjusted to one another such that, preferably, the product (in the case of grain kernels, an individual kernel) preferably moves less than 1/10 of the length of a kernel during the time of an individual measurement.

Especially for product types having a pronounced inhomogeneity, most particularly for regulating functions, for example, influencing the proportions of individual constituents, the invention has made its own testing method from one employed by the practical expert. The product is moved during observation and one sees the specimen often enough as if the material to be checked is viewed and evaluated from many sides while being held in the hands. In a particularly advantageous manner, the new process additionally allows overlapping sample zones to be measured. It is important, however, in any case, that a large number of measurements be performed. It has been found up to now as an empirical value that the number of individual measurements should be greater than 30.

According to another particularly advantageous development, all desired NIR wavelength ranges are measured simultaneously, preferably by the diode array principle. With this proposal, the accuracy of the measured values is increased, in particular, however, the main elements of the measuring device can remain stationary for the measurements. Essentially, no movable components are required.

In a further design, individual wavelength ranges are measured one after the other at short intervals and statistical analysis methods performed.

An additional preferred structural concept resides in that a continuous product stream is backed up and moved with respect to the measurement recorder while backed up.

That which was harmful during conventional employment of the NIR measuring technique is now, in contrast, used as an advantage in that the product is preferably moved in front of, respectively, passes in front of the measurement recorder.

In a mill, the product is constantly in motion for processing which now serves as the basis for the measurement in that, via statistical calculating methods, an enormous number of at least 10-15, preferably, however, more than 30 individual measurements are obtained from varying samples as well as over time and the desired average values calculated therefrom. Upon deviations from a desired value, this makes it possible to immediately intervene in the product flow or at individual processing stages since the error values are established within seconds.

The product back-up can be produced in a main or bypass pipe, preferably, however, by means of a dosing conveyor screw with regulated flow speed. The back-up can simultaneously be used to detect the product throughput.

The present invention further relates to a measuring apparatus for continuously detecting constituents of a product, particularly of a pourable foodstuff, with an NIR measuring device. It is characterized in that it has a through measuring section, an NIR measurement recording device, preferably for a series of measurements and a respective measuring time of less than 100, preferably less than 50 milliseconds, and a computer for the statistical calculation of average values for the respective constituents. In an especially preferred design, a diode array is used for the simultaneous detection of individual spectral regions.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein.

DETAILED DESCRIPTION OF THE PRESENTLY PREFERRED EXEMPLARY EMBODIMENTS

Figure 1:
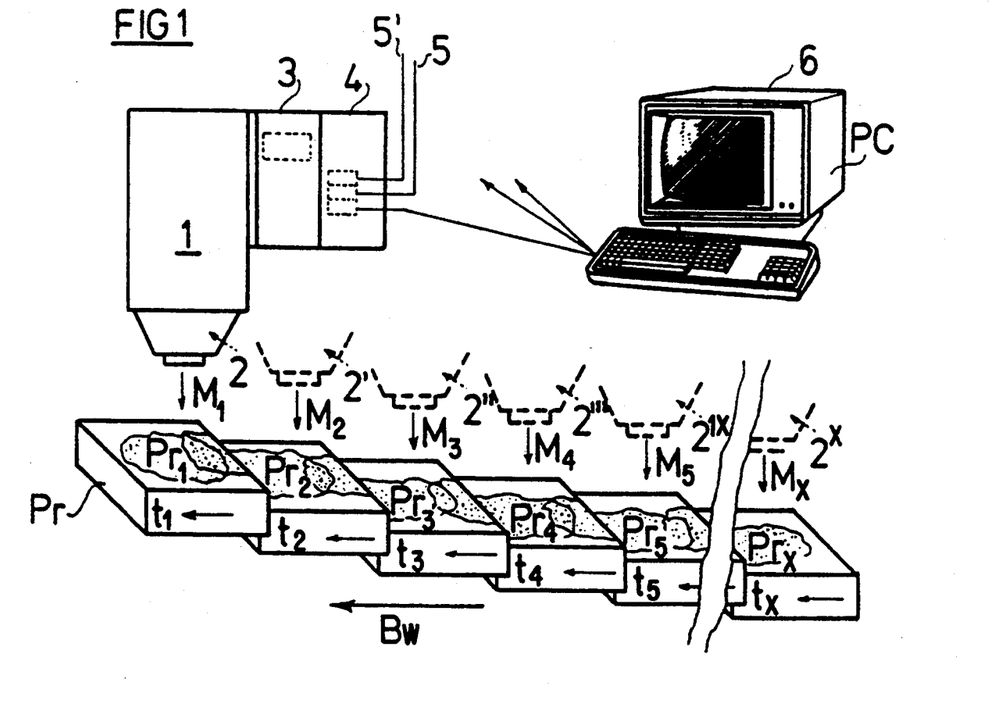
FIG. 1 schematically illustrates a complete measurement recorder with processing of the measured values.

Referring to FIG. 1, a measurement recorder 1 with an optical system has a measuring head 2 arranged directly above a sample Pr.

An electronic control system 3 includes a transducer unit 4 for the transmission of signals 5,5' and is connected to the measurement recorder 1 and is connected to a computer unit PC,6. FIG. 1 is intended to illustrate a pattern of motion in that the product is continuously moved from right to left according to arrow Bw.

The measuring head 2,2',2",2''',2'v,2x is drawn several times, however, in broken lines, over a respective different product batch Pr1,Pr2,Pr3,Pr4,Pr5,Prx. In reality, the sample Pr shifts itself in front of the stationary measuring head 2 and a respective measurement M1,M2,M3,M4,M5,Mx is made at the time t1,t2,t3,t4,t5,tx. It is important that the time required for the individual measurement, that is, for M1, for M2, etc., be carried out in the shortest possible time in the sense of a "flash recording". The individual flash recordings M1,M2,M3,M4,M5,Mx are transferred, via the optical system and the electronic control system, to the computer PC for statistical averaging of the series of measurements, for example, over a period of less than 10 seconds. Depending upon the objective, the number of measurements per averaging can lie between several dozen and hundreds.

Measurement in the vicinity of the actual production is understood under the term "on-line". "On-line" still leaves it open as to whether the sample is completely removed from the fabricating element and is checked externally in the measuring apparatus.

"In-line" indicates specifically that the product is measured in the processing machine or feed pipe itself or in an actively operated bypass. With "in line", no sample removal takes place, at most a sample deflection and a return again. The general problem is known. For specimen removal, the question is the representativeness of the specimen during measurement "in-line", and the location of sample measurement particularly important.

Figure 2:
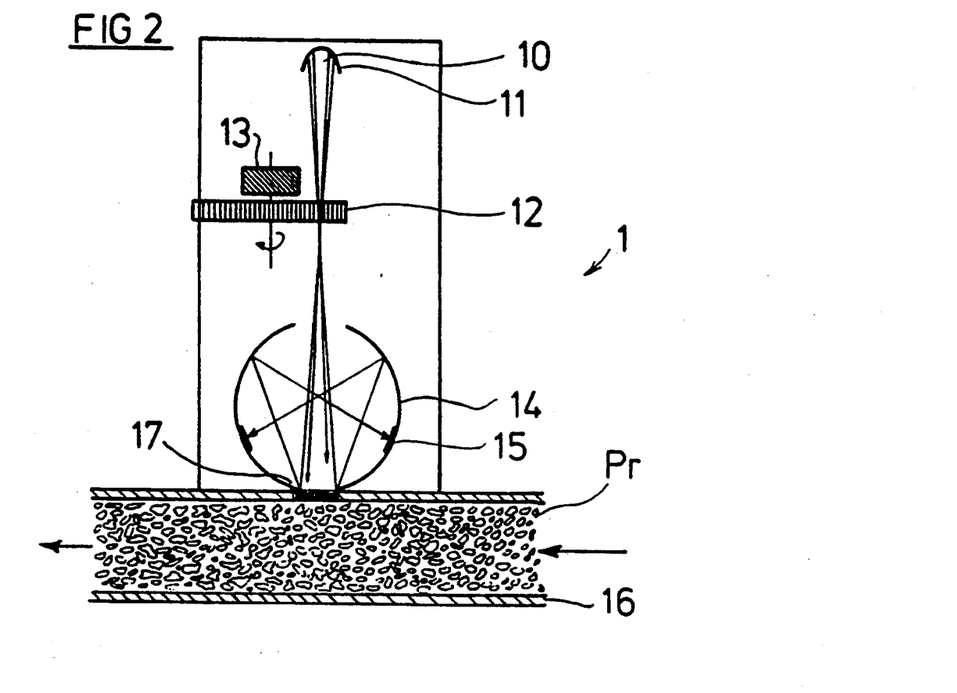
FIG. 2 shows the measurement recorder on an enlarged scale.

In FIG. 2, an NIR optical system is illustrated on an enlarged scale with a light source being identified by 10. Schematically, the measurement recorder 1 further has an ellipsoidal mirror (reflector) 11, a filter wheel 12 with a drive motor 13, additionally an Ulbricht sphere-type photometer 14, light receiver 15 and a product sample Pr, which is separated from the measurement recorder 1 by a window 17, and is compared with a calibrated reference. It is important for the filter wheel to rotate at a relatively high speed of more than 10, preferably more than 25, revolutions per second and to have, in the circumferential direction, a large number of filters, for example, 6, 12 or 24, through which the entire sought for light spectrum is detected every time.

Figure 3:
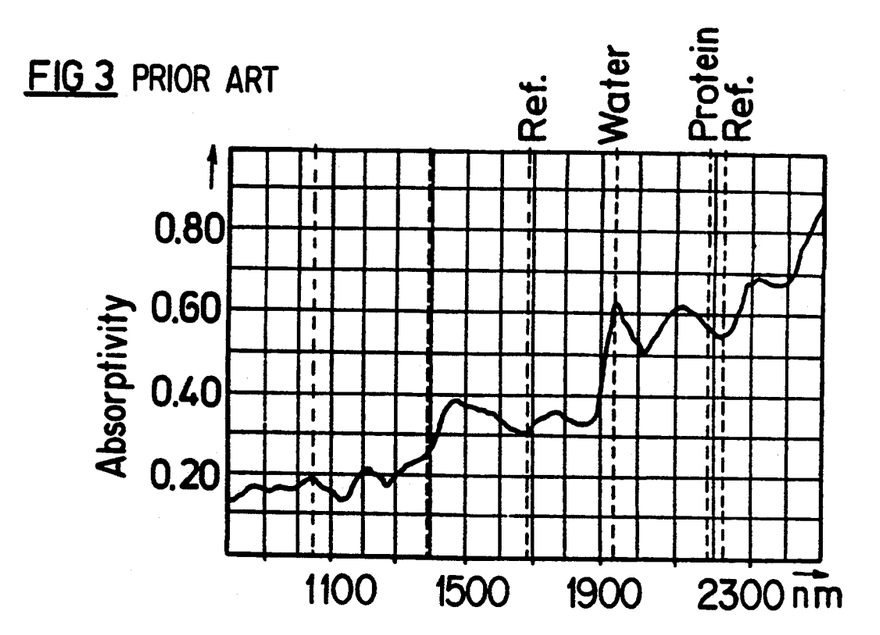
FIG. 3 shows an NIR absorption spectrum that is known per se.

FIG. 3 shows a known absorption spectrum of a flour-like commodity. The pair of values for both water and protein are recorded, the values for water lying above 1900 nm and those for protein in the example above 2200 nm.

Depending upon the degree of consolidation of the measuring device, the values for water and protein, respectively, the water content and the protein content can be determined simultaneously or one after the other in time, for instance, by selection of appropriate filters.

Figure 4:
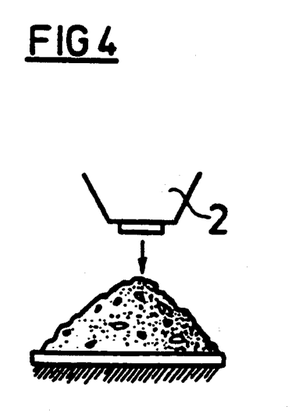
FIG. 4 figuratively shows an industrially unusable measurement of a random product movement.

FIG. 4 is intended to bring out that the experiments with the new invention have also confirmed the observation that measured values from a randomly poured pile do not provide representative values for the product as such since each pouring change produces a measuring error.

Figure 5:
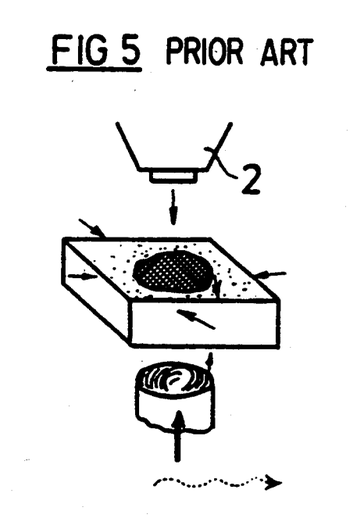
FIG. 5 shows a measuring principle of the prior art per European Patent Application No. 179 108.

FIG. 5 illustrates the method taught in the European Patent application No. 179 108 for controlled compaction of the sample to be measured. This method can be used successfully only with flour-like commodities.

Figure 6:
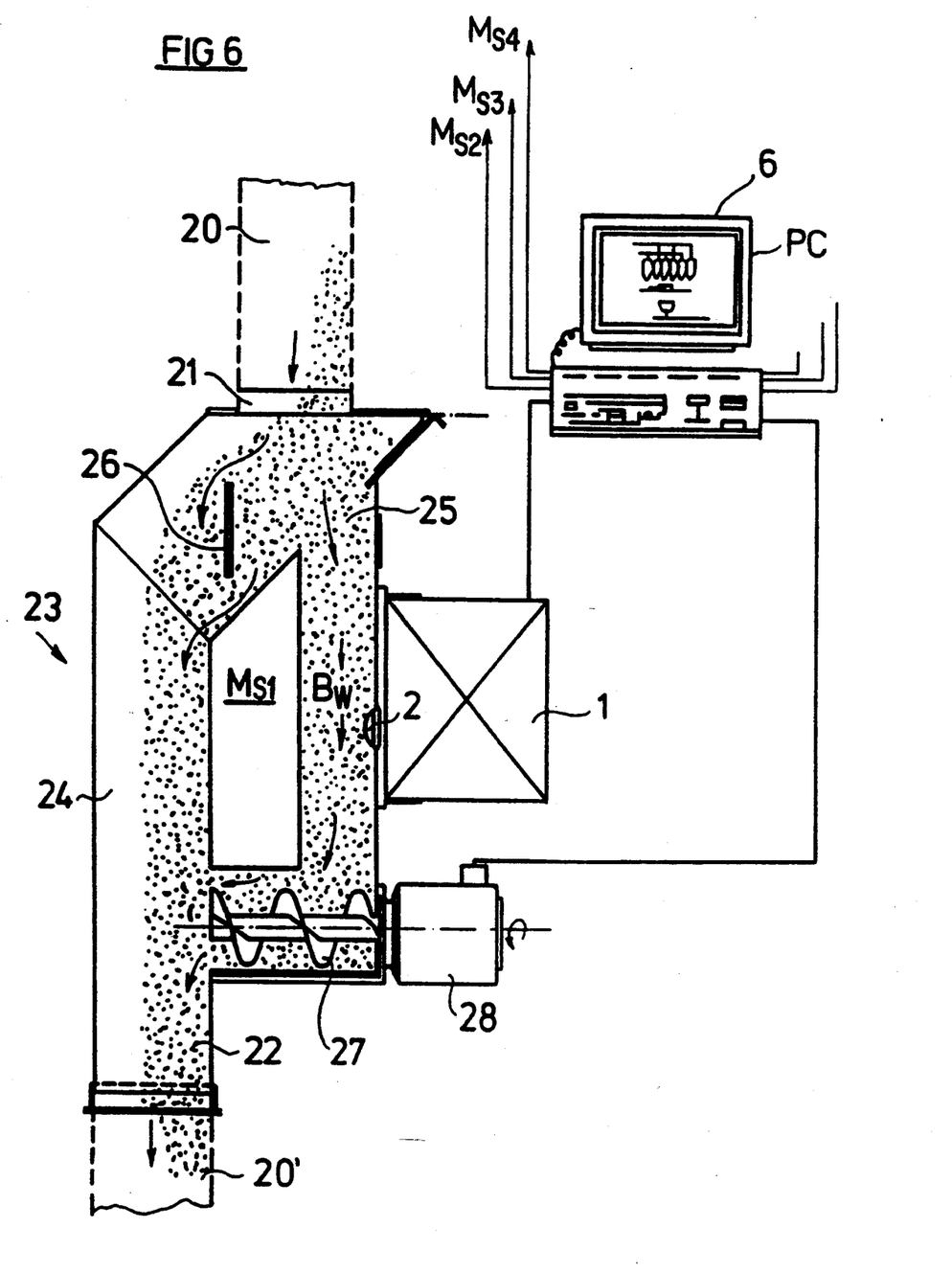
FIG. 6 shows an entire measuring section which is suitable for the measurement of whole kernels as well as for products which flow with difficulty.

FIG. 6 illustrates an entire measuring section which is part of a production feed pipe respectively 20,20', and has product admitting connection 21 above and a product discharging connection 22 below. The measuring section 23 is divided into a main feed pipe 24 and a bypass pipe 25. The main feed strand 24 has essentially the same cross section as the product feed pipe 20, 20', so that all of the product can flow through the main feed pipe 24 at maximum throughput. However, in order that a portion of the product stream is now forced to travel through the bypass, a baffle plate 26 is arranged in the transition region between the main feed pipe 24 and the bypass 25.

The feeding of the compact product stream in the vicinity of the measuring head 2 is assured by a regulated discharging screw conveyor 27. By selection of a very specific rotational speed, the discharging screw conveyor simultaneously provides for a constant descent of the product in the bypass, respectively, in the measuring channel 25. In this manner, one obtains a controllable or preselectable speed Bw for the product so that movement of the product can be adjusted to the specific situation. The present invention gives particularly good results for pourable commodities, such as whole grain kernels, which are friable per se. The discharging screw conveyor is controlled by the computer unit 6 via a drive motor 28 which preferably can be regulated in a stepless fashion.

Figure 7:
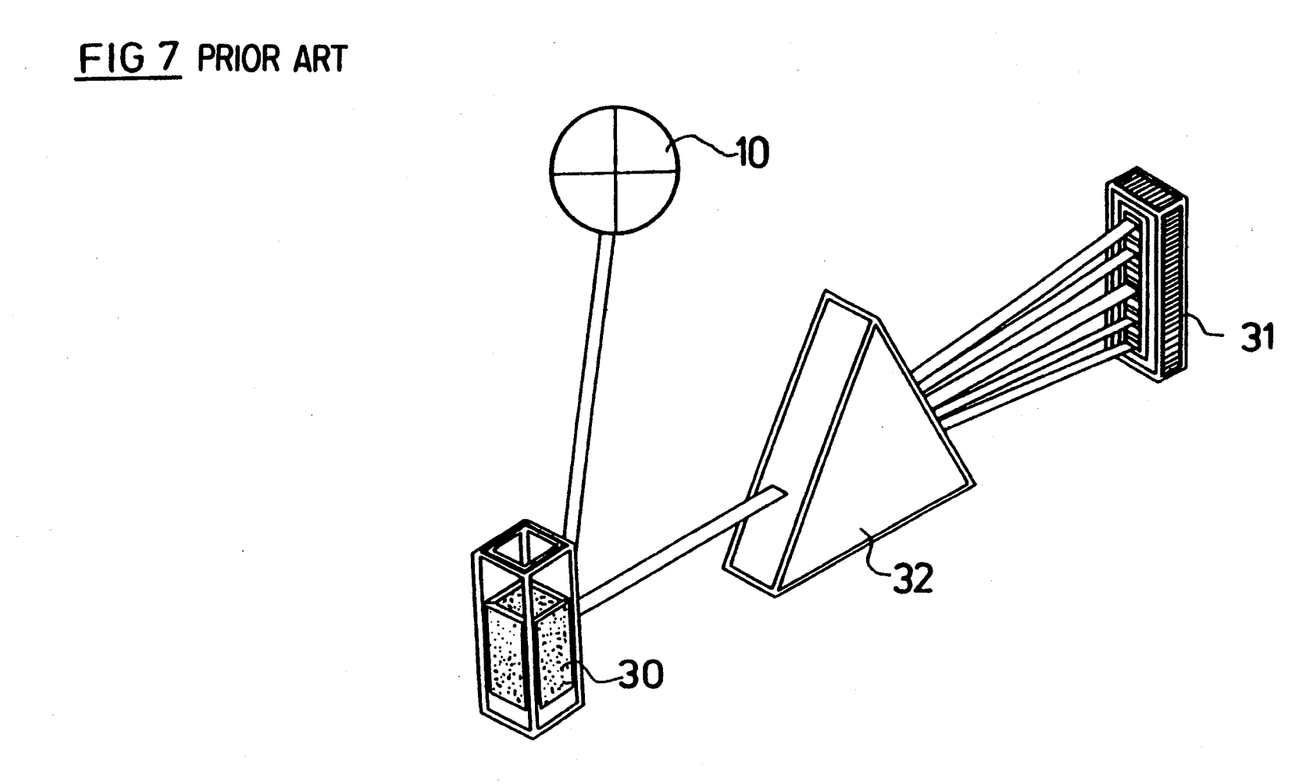
FIG. 7 schematically shows the diode array measuring principle, which is known per se.

FIG. 7 shows the use of the diode array principle, the apparatus having a sample channel 30, a light source 10 and a diode array detector 31. One can measure all desired wavelengths simultaneously with the diode array principle. The light to be analyzed is locally split up spectrally by means of a polychromator 32, respectively, a dispersion element and conducted to the diode array detector 31. The wavelength resolution can here be selected via the number of photosensitive diodes. The polychromator 32 (for example, a holographic grating) can be encased together with the diode array detector. The great advantage of this principle is that no movable components are required with the possible exception of a mirror to guide in a reference ray.

In all design variations, a complete computer unit can be assigned to an NIR measurement recording device, or several NIR measurement recording devices can be assigned to a common computer unit.

Depending on special applications, it can be advantageous to determine 1-second, 10-second or minute averages for the constituents. For regulating tasks, in particular, the second average provides great advantages while, in contrast, an averaging over longer measuring periods is advantageous for control purposes.

We claim:

1. A process for measuring the constituents of pourable food products utilizing light at NIR wavelengths comprising the steps of:
   directing a pourable food product in a continuous stream past an in-line measurement area;
   projecting light over a range of NIR wavelengths onto said food product as it moves past said in-line measurement area, said light being reflected from said food product;
   detecting the reflected light at a plurality of NIR wavelengths over said range of NIR wavelengths, for obtaining an in-line measurement of the reflected light at said plurality of wavelengths over said range, the step of detecting the reflected light over said range of NIR wavelengths occurring in a period of time not greater than 100 ms;
   repeating said steps of projecting light onto said moving food product and detecting the reflected light over said range of NIR wavelengths a predetermined number of times to obtain a predetermined number of in-line measurements of the reflected light at said plurality of wavelengths over said range;
   averaging the in-line measurements at corresponding wavelengths layer said range to obtain averaged values; and
   determining the constituents of the food product based on the averaged values obtained and a calibration value.

2. A process as claimed in claim 1, wherein said in-line measurement area includes a window adjacent to the food-product stream, and the step of projecting light over a range of NIR wavelengths includes projecting said light onto said food product as it moves past said window; and wherein the step of directing the food product in a continuous stream includes moving the food product at a controlled rate by a screw conveyor.

3. A process as claimed in claim 1, wherein the food product comprises grain kernels, and comprising the additional step of correlating the rate of movement of the food product past said measurement area with the step of detecting the reflected light at a plurality of NIR wavelengths over said range of NIR wavelengths so that a single kernel moves less than 1/10 of its length during said step of detecting.

4. A process as claimed in claim 1, wherein said step of repeating is performed a minimum of thirty times, thereby obtaining a minimum of thirty in-line measurements of the reflected light at said plurality of wavelengths over said range.

5. A process as claimed in claim 1, wherein the step of directing a pourable food product in a continuous stream includes moving the food product in a compact, homogeneous stream.

6. A process as claimed in claim 1, wherein the step of detecting the reflected light over said range of NIR wavelengths occurs in a period of time not greater than 50 ms.

7. A process as claimed in claim 6, wherein the step of directing a food product in a continuous stream past the in-line measurement area includes moving the food product at a controlled rate.

8. A process as claimed in claim 1, wherein the step of detecting the reflected light at a plurality of NIR wavelengths over said range of NIR wavelengths occurs substantially simultaneously.

9. A process as claimed in claim 8, further comprising the step of separating the reflected light into said plurality of wavelengths over said range and directing said separated light to a diode array detector for measurement of the reflected light at said plurality of wavelengths.

10. A process as claimed in claim 1, wherein the step projecting light over a range of NIR wavelengths includes projecting light at a plurality of specific wavelengths sequentially so that the detection of the reflected light occurs sequentially for the plurality of NIR wavelengths over said range.

11. A process as claimed in claim 10, wherein the step of projecting light at a plurality of NIR wavelengths includes rotating a filter wheel in the path of a light beam, said filter wheel having a plurality of NIR filters spaced thereon to permit projection of light at said specific wavelengths as said filter wheel is rotated.

12. A process as claimed in claim 11, wherein said plurality of filters includes a minimum of six filters spaced around said wheel And wherein said step of rotating the filter wheel includes rotating the filter wheel at greater than 25 revolutions per second.

13. A process as claimed in claim 1, wherein the step of directing a food product past said measurement area includes directing the food product through a pipe in a continuous, in-line stream substantially normal to the light projected onto said food product.

14. A process as claimed in claim 13, wherein the step of directing a food product through a pipe includes diverting the food product through a bypass pipe and regulating the rate of movement of the food product through said bypass pipe past said measurement area.

15. Apparatus for measuring the constituents of a pourable food product comprising:
a channel through which a pourable food product moves in a continuous stream;
an in-line measurement area located in said channel;
a NIR measuring device positioned adjacent to said in-line measurement area for the in-line measurement of the constituents of said pourable food product as said food product moves past said measurement area;
said NIR measuring device having means for projecting light onto said food product as it moves past said measurement area and for detecting reflected light at a plurality of NIR wavelengths over a preselected range of NIR wavelengths to provide a plurality of in-line measurements of the reflected light at said plurality of NIR wavelengths;
computer means for statistically averaging the plurality of measurements obtained and for determining the constituents of the food product; and
means for moving the pourable food product through said channel past said measurement area.

16. Apparatus as claimed in claim 15, wherein said means for detecting includes means for separating the reflected light into said plurality of wavelengths within said preselected range of NIR wavelengths, and a diode array detector for measuring the reflected light at said plurality of wavelengths.

17. Apparatus as claimed in claim 15, wherein said NIR measuring device provides a plurality of in-line measurements of the reflected light at said plurality of NIR wavelengths, the time of each in-line measurement being not greater than 50 ms.

18. Apparatus as claimed in claim 15, wherein said channel includes a pipe for carrying said pourable food product in a continuous stream, and said in-line measurement area includes a window in said pipe adjacent to the food-product stream through which said light is projected onto said food product.

19. Apparatus as claimed in claim 18, wherein said means for moving the pourable food product controls the rate of movement of said, food product through said pipe.

20. Apparatus as claimed in claim 19, wherein said means for moving, the pourable food product comprises a screw conveyor and a drive motor for said screw conveyor controlled by said computer means.

21. Apparatus as claimed in claim 18, wherein said NIR measuring device includes a light source, a rotatable filter wheel, and a plurality of NIR filters spaced thereon to permit projection of light at specific NIR wavelengths through said window as said filter wheel rotates.

22. Apparatus as claimed in claim 21, wherein said NIR measuring device further comprises a motor for driving said filter wheel at above twenty-five revolutions per second.

23. A process for measuring at NIR wavelengths at least one constituent of a flowable particulate substance during in-line processing of the substance, comprising:
advancing said particulate substance in a continuous stream along a predetermined path during said in-line processing of said substance;
projecting light over a range of NIR wavelengths onto different sample zones of said particulate substance as they flow past a predetermined location in said path, said light being reflected from said sample zones;
detecting the reflected light from said sample zones of particulate substance at a plurality of NIR wavelengths over said range of NIR wavelengths, and measuring the reflected light at said plurality of wavelengths over said range, the detection of the reflected light: over this range of NIR wavelengths occurring in a period of time not greater than 100 ms;

repeating the steps of projecting light at said NIR wavelengths onto different sample zones of said particulate substance and detecting the light reflected therefrom until detection over said range of NIR wavelengths has occurred a minimum of thirty times, thereby obtaining a minimum of thirty repeated measurements of the reflected light at said plurality of wavelengths over said range;

obtaining the mean value of the measurements obtained; and determining the value of at least one constituent of the flowable particulate substance during in-line processing using the mean value obtained.

24. A process as claimed in claim 23, wherein the step of detecting the reflected light over the range of NIR wavelengths occurs in a period of time not greater than 50 ms.

25. A process as claimed in claim 23, wherein said step of obtaining the mean value is performed statistically.

26. A process as claimed in claim 25, wherein the step of determining is performed using the mean value and a calibration value.

27. A process as claimed in claim 23, wherein the step of projecting light over a range of NIR wavelengths onto different sample zones includes projecting light at a plurality of specific NIR wavelengths sequentially, and the step of detecting the reflected light occurs sequentially for the plurality of specific NIR wavelengths over said range.

28. A process as claimed in claim 27, wherein the step of projecting light at a plurality of NIR wavelengths includes rotating a filter wheel in the path of a light beam, said filter wheel having a plurality of NIR filters spaced thereon to permit projection of light at said specific NIR wavelengths as said filter wheel is rotated, the range of NIR wavelengths being the range of wavelengths encompassed by the NIR filters in the filter wheel.

29. A process as claimed in claim 28, wherein said plurality of filters includes a minimum of six filters spaced around said wheel and wherein said step of rotating the filter wheel includes rotating the filter wheel at greater than 25 revolutions per second.

30. A process as claimed in claim 23, wherein said particulate substance comprises a foodstuff.

31. A process as claimed in claim 30, wherein the step of advancing said foodstuff in a continuous stream includes moving the foodstuff in a compact, homogeneous stream.

32. A process as claimed in claim 30 further comprising the step of determining the throughput of the foodstuff during in-line processing of the foodstuff.

33. A process as claimed in claim 30, wherein more than one constituent of a foodstuff is measured.

34. A process as claimed in claim 30, wherein said predetermined path includes a window adjacent to the stream of foodstuff, and the step of projecting light over a range of NIR wavelengths includes projecting said light onto different sample zones of said foodstuff as they flow past said window; and wherein the step of advancing said foodstuff in a continuous stream includes moving the foodstuff at a controlled rate so that each of the sample zones flows past said window at substantially the same speed.

35. A process as claimed in claim 34, wherein the foodstuff comprises grain kernels, and comprising the additional step of correlating the rate of movement of the grain kernels past said window with the step of detecting the reflected light at a plurality of NIR wavelengths over said range of NIR wavelengths so that a single kernel moves less than 1/10 of its length during said step of detecting.

36. A process as claimed in claim 30, wherein the step of advancing a foodstuff includes directing the foodstuff through a pipe in a continuous, in-line, compact, homogeneous stream substantially normal to the light projected onto said foodstuff.

37. A process as claimed in claim 36, wherein the step of directing of a foodstuff through a pipe includes diverting the foodstuff through a bypass pipe and regulating the rate of movement of the foodstuff through said bypass pipe.

38. A process as claimed in claim 30, wherein said measuring process is conducted at each of two, separate, in-line locations, one measuring process being conducted on unrefined foodstuff and the other measuring process being conducted on refined foodstuff.

39. A process as claimed in claim 38, wherein said unrefined foodstuff is unground grain and said refined foodstuff is flour.

* * * * *

UNITED STATES PATENT AND TRADEMARK OFFICE
CERTIFICATE OF CORRECTION

PATENT NO. : 5,406,084
DATED : April 11, 1995
INVENTOR(S) : Hans Tobler and Peter Perten It is certified that error appears in the above-indentified patent and that said Letters Patent is hereby corrected as shown below:

On the title page: Item

[30] Delete "[CH] Switzerland" and insert --[SE] Sweden--.

Abstract, line 11, delete "," after "usable".

Claim 1, column 6, line 56, delete "layer", and insert --over--.

Claim 12, column 7, line 51, delete "And" and insert --and--.

Claim 19, column 8, line 37, delete "," after "said".

Claim 20, column 8, line 40, delete "," after "moving".

Claim 23, column 9, line 1, delete ":" after "light".
Column 10,
Delete claims 38 and 39.

Signed and Sealed this

Eighteenth Day of July, 1995

Attest:

BRUCE LEHMAN

*Attesting Officer*     *Commissioner of Patents and Trademarks*